United States Patent
Yanagisawa et al.

(10) Patent No.: US 7,154,107 B2
(45) Date of Patent: *Dec. 26, 2006

(54) PARTICLE BEAM IRRADIATION SYSTEM AND METHOD OF ADJUSTING IRRADIATION FIELD FORMING APPARATUS

(75) Inventors: Masaki Yanagisawa, Hitachi (JP); Hiroshi Akiyama, Hitachiohta (JP); Koji Matsuda, Hitachi (JP); Hisataka Fujimaki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/090,206

(22) Filed: Mar. 28, 2005

(65) Prior Publication Data

US 2005/0167616 A1 Aug. 4, 2005

Related U.S. Application Data

(62) Division of application No. 11/006,605, filed on Dec. 8, 2004.

(30) Foreign Application Priority Data

Dec. 10, 2003 (JP) ............................. 2003-411344

(51) Int. Cl.
*H05H 9/00* (2006.01)
(52) U.S. Cl. ..................... 250/492.3; 315/501; 607/2
(58) Field of Classification Search ............. 250/492.3; 315/501, 505, 507
See application file for complete search history.

(56) References Cited

U.S. PATENT DOCUMENTS

| | | | |
|---|---|---|---|
| 5,039,867 A | 8/1991 | Nishihara et al. | |
| 5,969,367 A | 10/1999 | Hiramoto et al. | |
| 6,087,672 A | 7/2000 | Matsuda et al. | |
| 6,265,837 B1 | 7/2001 | Akiyama et al. | |
| 6,316,776 B1 | 11/2001 | Hiramoto et al. | |
| 6,597,005 B1 | 7/2003 | Badura et al. | |
| 6,600,164 B1 * | 7/2003 | Badura et al. | 250/492.3 |
| 6,617,598 B1 | 9/2003 | Matsuda | |

(Continued)

FOREIGN PATENT DOCUMENTS

DE 199 07 098 A1 8/2000

(Continued)

OTHER PUBLICATIONS

Chu, W T et al., "Instrumentation for Treatment of Cancer Using Proton and Light-Ion Beams", Review of Scientific Instruments, Aug. 1, 1993, pp. 2074-2079, vol. 64, No. 8, American Institute of Physics, New York, US.

(Continued)

*Primary Examiner*—David A. Vanore
(74) *Attorney, Agent, or Firm*—Dickstein Shapiro LLP

(57) ABSTRACT

A particle therapy system, as one example of a particle beam irradiation system, comprises a charged particle beam generator and an irradiation field forming apparatus. An ion beam from the charged particle beam generator is irradiated to a diseased part in the body of a patient through the irradiation field forming apparatus. A scattering compensator and a range modulation wheel (RMW) are disposed on the upstream side in a direction of beam advance and are movable along a beam axis. The movement of the scattering compensator and the RMW adjusts a size of the ion beam entering a scatterer device, whereby a change in scattering intensity of the ion beam in the scatterer device is adjusted. As a result, a penumbra in dose distribution is reduced and a more uniform dose distribution in a direction perpendicular to the direction of beam advance is obtained in the diseased part.

6 Claims, 7 Drawing Sheets

U.S. PATENT DOCUMENTS

| | | | |
|---|---|---|---|
| 6,777,700 B1 * | 8/2004 | Yanagisawa et al. | .... 250/492.3 |
| 2003/0160189 A1 | 8/2003 | Matsuda | |
| 2004/0149934 A1 * | 8/2004 | Yanagisawa et al. | .... 250/492.3 |

FOREIGN PATENT DOCUMENTS

| | | |
|---|---|---|
| EP | 0779081 | 6/1997 |
| EP | 0 826 392 A2 | 3/1998 |
| EP | 1 041 579 A1 | 10/2000 |
| EP | 1 371 390 | 12/2003 |
| JP | 10-199700 | 7/1998 |
| JP | 10-211292 | 8/1998 |
| JP | 2000-202047 | 7/2000 |
| WO | WO 00/49624 | 8/2000 |

OTHER PUBLICATIONS

"Review of Scientific Instruments," Vol. 64, No. 8, (Aug. 1993, pp. 2074-2086).

* cited by examiner

DIRECTION OF ADVANCE OF ION BEAM

FIG. 6

| REQUIRED PENETRATION DEPTH | SCATTRING COMPENSATOR + RMW | INCIDENT ENERGY | RANGE ADJUSTER THICKNESS | SCATTRING COMPENSATOR + RMW Z-AXIS POSITON |
|---|---|---|---|---|
| [cmWEQ] | [ID] | [MeV] | [cmWEQ] | [mm] |
| 35.0 | 1 | 250 | 0.0 | 3060 |
| 34.9 | | | 0.1 | 3061 |
| : | | | : | : |
| 29.0 | | | 6.0 | 3120 |
| 28.9 | 2 | 225 | 0.0 | 3085 |
| : | | | : | : |
| 24.0 | | | 4.9 | 3115 |
| 23.9 | 3 | 200 | 0.0 | 3072 |
| : | | | : | : |
| 20.0 | | | 3.9 | 3120 |
| 19.9 | 4 | 180 | 0.0 | 3078 |
| : | | | : | : |
| 16.0 | | | 3.9 | 3120 |
| 15.9 | 5 | 160 | 0.0 | 3080 |
| : | | | : | : |
| 13.0 | | | 2.9 | 3112 |
| 12.9 | 6 | 140 | 0.0 | 3075 |
| : | | | : | : |
| 10.0 | | | 2.9 | 3111 |
| 9.9 | 7 | 120 | 0.0 | 3080 |
| : | | | : | : |
| 7.0 | | | 2.9 | 3120 |
| 6.9 | 8 | 100 | 0.0 | 3080 |
| : | | | : | : |
| 5.0 | | | 1.9 | 3120 |
| 4.9 | 9 | 85 | 0.0 | 3080 |
| : | | | : | : |
| 3.1 | | | 1.3 | 3119 |
| 3.5 | | | 1.4 | 3120 |

PARTICLE BEAM IRRADIATION SYSTEM AND METHOD OF ADJUSTING IRRADIATION FIELD FORMING APPARATUS

CROSS-REFERENCE TO RELATED APPLICATIONS

This application is a divisional of U.S. patent application Ser. No. 11/006,605, filed on Dec. 8, 2004. The subject matter of the prior application is incorporated in its entirety by reference herein.

BACKGROUND OF THE INVENTION

1. Field of the Invention

The present invention relates to a particle beam irradiation system and a method of adjusting an irradiation field forming apparatus. More particularly, the present invention relates to a particle beam irradiation system suitable for use as a particle therapy system for irradiating a charged particle beam, such as a proton or carbon ion beam, to a diseased part (cancer) for treatment, a material irradiation system for irradiating a charged particle beam to materials, a food irradiation system for irradiating a charged particle beam to foods, and a radio isotope producing system utilizing a charged particle beam.

2. Description of the Related Art

A known particle therapy system comprises a charged particle beam generator, a beam transport system, and a rotating irradiation apparatus. The charged particle beam generator includes a synchrotron (or a cyclotron) as an accelerator. A charged particle beam (hereinafter referred to as an "ion beam") accelerated by the synchrotron to a level of setting energy reaches the irradiation apparatus through the beam transport system (hereinafter referred to as a "first beam transport system"). The rotating irradiation apparatus comprises an irradiation-apparatus beam transport system (hereinafter referred to as a "second beam transport system"), an irradiation field forming apparatus, and a rotating apparatus (gantry) for rotating the second beam transport system and the irradiation field forming apparatus in union. After passing the second beam transport system, the ion beam is irradiated to a diseased part (cancer) in the body of a patient through the irradiation field forming apparatus.

The irradiation field forming apparatus serves not only to shape the ion beam extracted from the charged particle beam generator in match with the three-dimensional shape of the diseased part as an irradiation target, thereby forming an irradiation field, but also to adjust the irradiation dose in the irradiation field. As a method for irradiating the desired irradiation dose in match with the shape of the irradiation target, there is known a double scattering method in which two types of scatterers arranged in a spaced relation with a certain distance between them in the axial direction of the ion beam are employed to make the irradiation dose of the ion beam uniform by utilizing the fact that the ion beam after passing through the scatterer has a substantially normal distribution (see, e.g., FIG. 36 in p. 2081 of Non-Patent Reference 1: REVIEW OF SCIENTIFIC INSTRUMENTS, Volume 64, Number 8 (August 1993), pp. 2074–2086). As other irradiation methods, there are also known a wobbling method (see, e.g., Patent Reference 1: JP,A 10-211292 and Patent Reference 2: JP,A 2000-202047) and a scanning method (see, e.g., Patent Reference 3: JP,A 10-199706), in which two scanning magnets are used to make the irradiation dose of the ion beam uniform.

In those irradiation methods, a Bragg peak spreading-out device (SOBP device) is employed to make the irradiation dose of the ion beam uniform in the direction of depth of the diseased part in the patient body (i.e., in the irradiating direction of the ion beam). The SOBP device is of a structure having areas that differ in thickness and are formed on a plane perpendicular to the direction of advance of the ion beam. By causing the ion beam to pass through the areas having different thicknesses, the ion beam has plural energy components. Also, by setting a size of the area having each thickness, a weight of each energy component of the ion beam is determined. Then, a dose distribution having high uniformity in the direction of advance of the ion beam is formed by superimposing those plural energy components so as to properly adjust the dose distribution. Known examples of such an SOBP device include a ridge filter (see FIG. 31 in p. 2078 and FIG. 41 in p. 2084 of Non-Patent Reference 1), a range modulation wheel (see FIG. 30 in p. 2077 of Non-Patent Reference 1), etc.

Because those SOBP devices have, as described above, the structure having areas that differ in thickness and are formed on a plane perpendicular to the direction of advance of the ion beam, the scattering intensity of the ion beam in the SOBP device differs depending on the areas through which the ion beam passes. To suppress the influence of the scattering, it has hitherto been proposed to arrange the SOBP device at a position within the irradiation field forming apparatus on the most downstream side in the direction of advance of the ion beam. Alternatively, when the SOBP device is arranged on the upstream side, a scattering compensator is disposed to compensate for differences in the scattering intensity of the ion beam among the respective areas of the SOBP device.

SUMMARY OF THE INVENTION

However, the above-described related art has problems given below.

When the SOBP device is arranged on the downstream side in the direction of advance of the ion beam, the effective beam distance up to the irradiation position (i.e., the diseased part) reduces and a blur (penumbra) in the irradiation dose distribution spreading beyond the irradiation target increases correspondingly. Further, the beam size increases and hence the apparatus size also increases. On the other hand, when the SOBP device is arranged on the upstream side, the penumbra can be reduced, but uniformity of the dose distribution in a direction perpendicular to the direction of advance of the ion beam is difficult to keep high because of an increase of influences upon, e.g., a change in incident energy of the ion beam and a change in thickness of an ion beam passage area within a range adjusting device that is arranged on the downstream side to vary the range of the ion beam.

Accordingly, it is an object of the present invention to provide a particle beam irradiation system and a method of adjusting an irradiation field forming apparatus, which can produce a more uniform dose distribution in a direction perpendicular to the direction of advance of the ion beam.

To achieve the above object, the present invention is featured in that a scattering compensator for compensating differences in scattering intensity of a charged particle beam in a Bragg peak spreading-out device is provided on the Bragg peak spreading-out device, and the Bragg peak spreading-out device and the scattering compensator are mounted in an irradiation field forming apparatus movably in a direction of advance of the charged particle beam. In other words, by providing the scattering compensator on the Bragg peak spreading-out device, the Bragg peak spreading-out device and the scattering compensator can be arranged on the upstream side in the direction of beam advance, and a penumbra in dose distribution can be reduced with such an arrangement. Further, since the Bragg peak spreading-out device and the scattering compensator are movable in the direction of beam advance, a dose distribution of the charged particle beam at an irradiation target position in a direction perpendicular to the direction of beam advance can be made more uniform by optimally adjusting the position of the Bragg peak spreading-out device and the scattering compensator.

Thus, according to the present invention, it is possible to reduce the penumbra, and to produce a more uniform dose distribution at the irradiation target position of the charged particle beam in the direction perpendicular to the direction of beam advance.

BRIEF DESCRIPTION OF THE DRAWINGS

FIG. 6 is a table showing irradiation condition information stored in a memory of an irradiation controller shown in FIG. 2;

FIGS. 7A to 7C each show a dose distribution at an irradiation target in a direction perpendicular to the direction of beam advance, in which FIG. 7A represents a state in which scattering intensity is in balance, FIG. 7B represents a state in which scattering intensity is out of balance due to lowering of incident energy or an increase in thickness of the range adjusting device, and FIG. 7C represents a state in which the dose distribution is made uniform by moving a scattering compensator and the RMW in the direction of beam advance.

DESCRIPTION OF THE PREFERRED EMBODIMENTS

Figure 1:
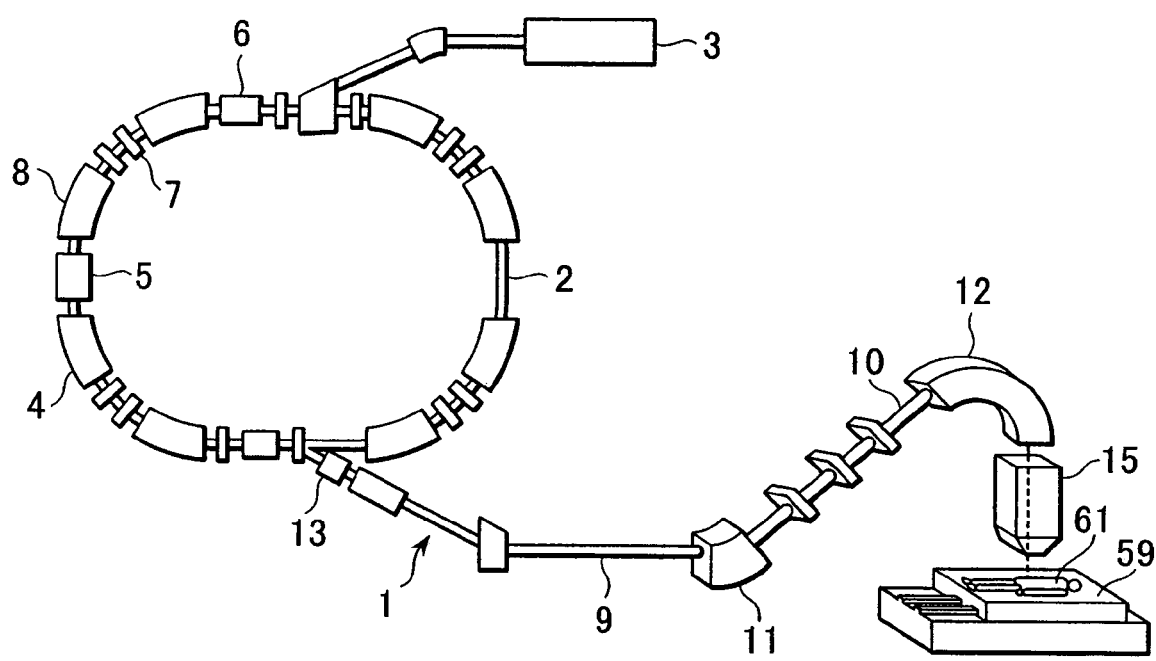
FIG. 1 is a schematic view of a particle therapy system according to one preferable embodiment, i.e., a first embodiment, of the present invention.

A particle therapy system as one preferable embodiment of the present invention will be described below with reference to FIG. 1. A particle therapy system 1 of this embodiment comprises a charged particle beam generator 2 and an irradiation field forming apparatus (as irradiation apparatus) 15. The charged particle beam generator 2 comprises an ion source (not shown), a pre-accelerator 3, and a synchrotron 4. Ions (e.g., proton or carbon ions) generated by the ion source are accelerated by the pre-accelerator (e.g., a linear accelerator) 3. An ion beam emitted from the pre-accelerator 3 enters the synchrotron 4. The ion beam is accelerated in the synchrotron 4 in which energy is given to the ion beam with radio-frequency (RF) power applied from an RF cavity 5. After energy of the ion beam circulating in the synchrotron 4 has been increased up to a setting level, an RF wave is applied to the circulating ion beam from an RF knockout electrode 6 for beam extraction. With the application of the RF wave, the ion beam circulating within a separatrix is forced to transit to the outside of the separatrix and to exit from the synchrotron 4 through a beam extraction deflector 13. At the time of extracting the ion beam, currents supplied to magnets, such as quadrupole magnets 7 and bending magnets 8, disposed in the synchrotron 4 are held at setting values, and therefore the separatrix is also held substantially constant. The extraction of the ion beam from the synchrotron 4 is stopped by ceasing the application of the RF power to the RF knockout electrode 6.

The ion beam extracted from the synchrotron 4 is transported to the irradiation field forming apparatus 15, serving as an irradiation system, through an ion beam transport system 9. An inverted U-shaped section 10 as a part of the ion beam transport system 9 and the irradiation field forming apparatus 15 are mounted in a rotating gantry (not shown). The inverted U-shaped section 10 includes bending electrodes 11, 12. The ion beam is irradiated from the irradiation field forming apparatus 15 to a diseased part 62 (see FIG. 2) in the body of a patient 61 lying on a treatment couch (bed) 59.

Figure 2:
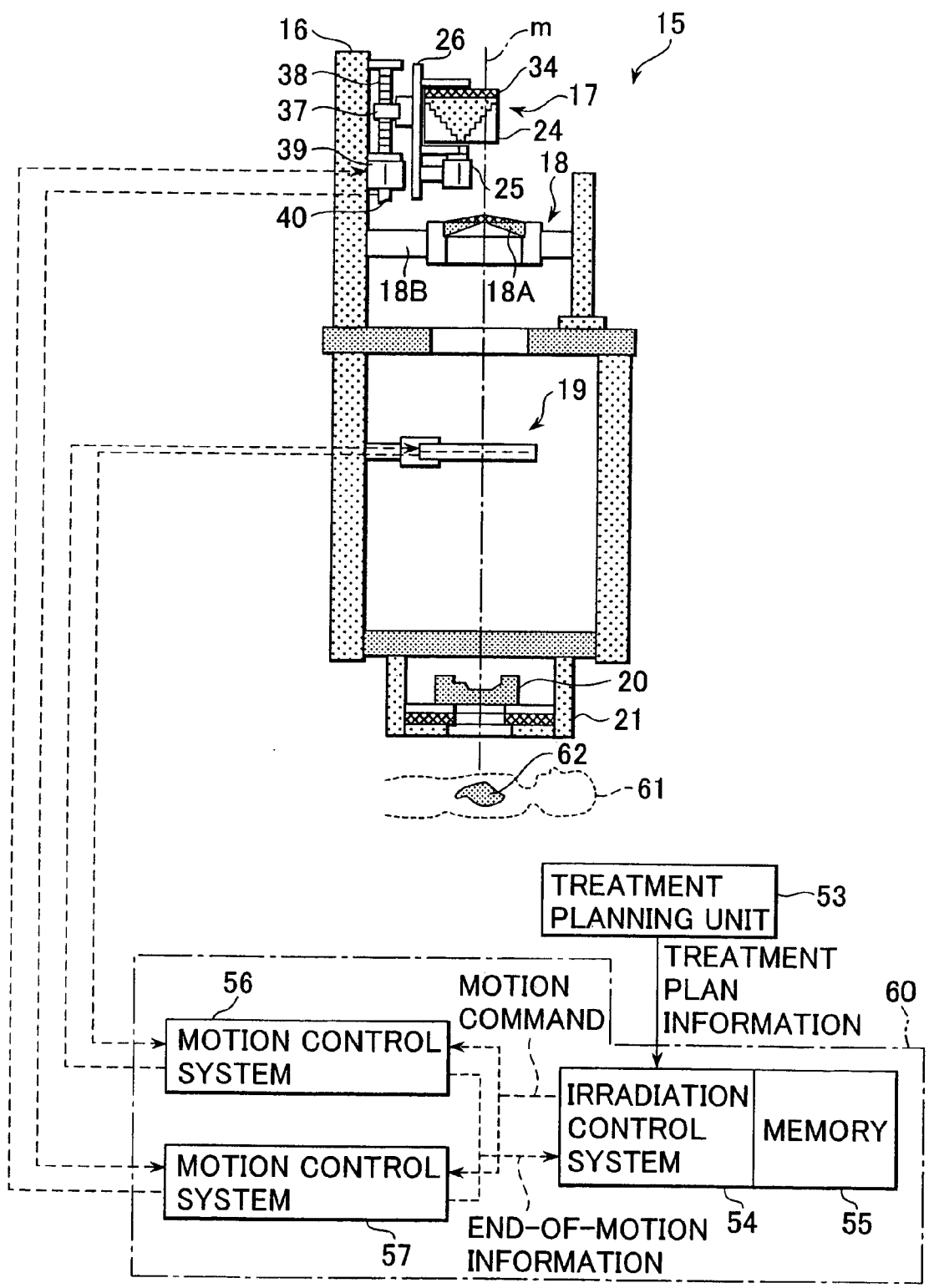
FIG. 2 is a vertical sectional view of an irradiation field forming apparatus shown in FIG. 1.

A detailed structure of the irradiation field forming apparatus 15 used in this embodiment will be described below with reference to FIG. 2. The irradiation field forming apparatus 15 is a double scattering apparatus. The irradiation field forming apparatus 15 has a casing 16 mounted to the inverted U-shaped section 10. A first scatterer 17, a range modulation wheel (RMW) device (also called a Bragg peak spreading-out device) 17, a scatterer device 18, a range adjusting device 19, a compensator (bolus) 20, and a an aperture collimator 21 are arranged within the casing 16 successively in this order from the upstream side in the direction of advance of the ion beam (i.e., in the direction of a beam axis m).

Figure 3:
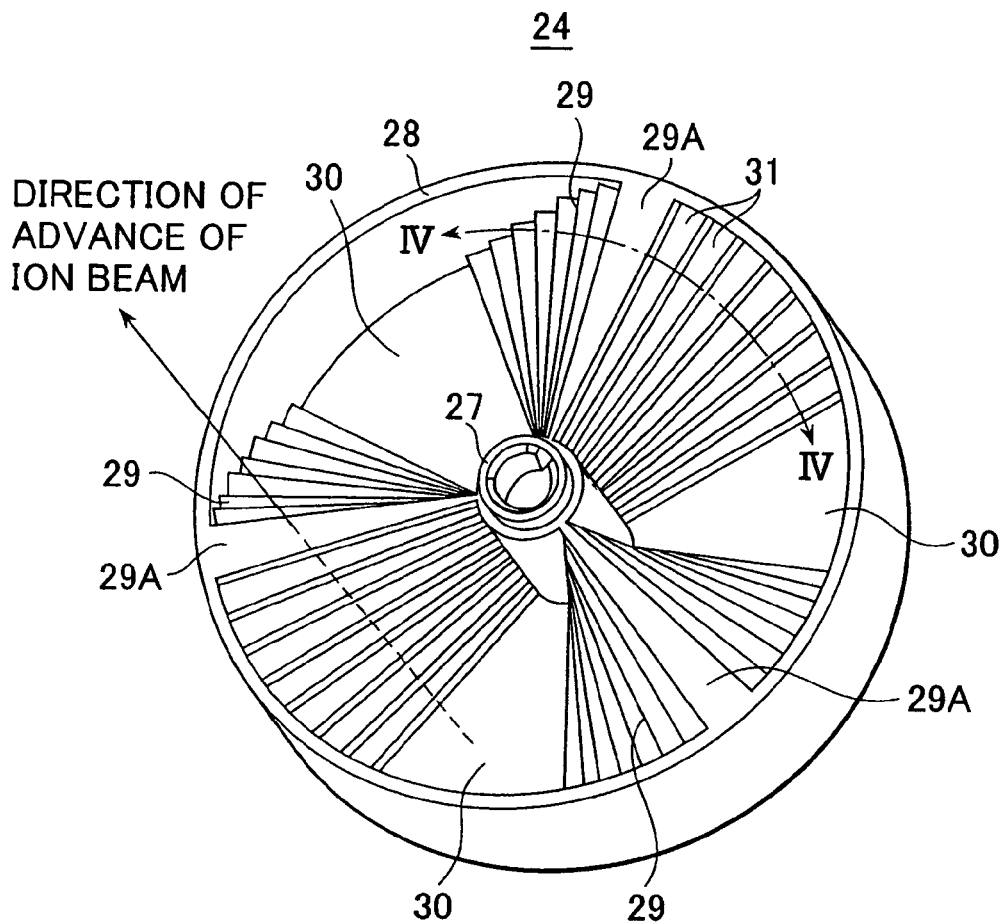
FIG. 3 is a perspective view showing the structure of an RMW.

The RMW device 17 comprises an RMW 24, a motor 25 for rotating the RMW 24, and an RMW support member 26 for supporting both the RMW 24 and the motor 25. FIG. 3 shows a detailed structure of the RMW 24. As shown in FIG. 3, the RMW 24 comprises a rotating shaft 27, a cylindrical member 28 disposed in a concentric relation to the rotating shaft 27, and a plurality (three in this embodiment) of blades (blade portions) 29 each of which is joined to the rotating shaft 27 and is extended in the radial direction of the RMW 24. The blades 29 are each formed to have a circumferential width increasing toward the outer side in the radial direction (namely, to have a larger circumferential width on the outer side nearer to the cylindrical member 28 than the inner side nearer to the rotating shaft 27). An outer end of the blade 29 is joined to an inner circumferential surface of the cylindrical member 28. Furthermore, an opening 30 is formed between every two blades 29 in the circumferential direction of the RMW 24. In other words, one RMW 24 has three openings 30 formed between adjacent two of the three blades 29. The opening 30 is also formed such that its circumferential width gradually increases toward the outer side in the radial direction.

Each of the blades 29 has a plurality of plane areas 31 arranged in the form of stairs in the circumferential direction of the RMW 24 (namely, plane areas 31 correspond to, e.g., flat surfaces of stairs on which feet are rested when stepping up and down). Each of the plane areas 31 has a different thickness relative to a bottom surface of the RMW 24 in the direction of beam advance (in other words, levels of the plane areas 31 relative to the bottom surface of the RMW 24 differ from one another). The thickness of each plane area 31 is called here the plane area thickness. More specifically, each blade 29 is formed such that the plane area thickness of the blade 29 increases in a stepwise way from each of the plane areas 31 adjacent to the openings 30, which are positioned on both sides of the relevant blade 29 in the circumferential direction, toward the plane area 31 positioned at a blade top portion 29A having the largest thickness in the direction of beam advance. Each plane area 31 is extended from the rotating shaft 27 toward the cylindrical member 28 and has a circumferential width gradually increasing toward the outer side in the radial direction.

With the above-described structure of the RMW 24, the ion beam having passed through the RMW 24 has plural energy components corresponding to the respective thicknesses of the plane areas 31 through which the ion beam has passed. As a result, the Bragg peak (BP) is spread out so that the irradiation dose is uniform in the direction of beam advance (i.e., in the direction of depth of the diseased part 62 in the body of the patient 61).

Figure 4:
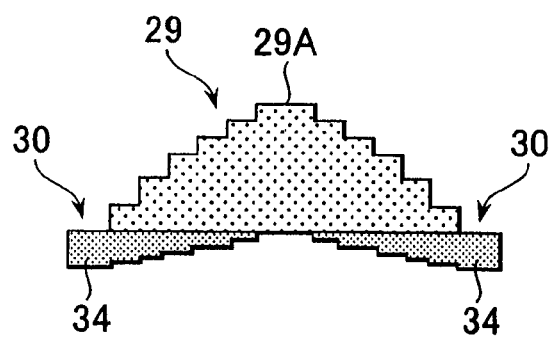
FIG. 4 is a sectional view taken along a line IV—IV in FIG. 3.

Returning to FIG. 2, a scattering compensator (scattering compensation device) 34 is integrally joined to a surface of the RMW 24 on the upstream side in the direction of beam advance (i.e., on a bottom surface of the RMW 24). FIG. 4 is a sectional view of the blade 29 of the RMW 24 (corresponding to a section taken along a line IV—IV in FIG. 3), the view showing a general structure of the scattering compensator 34 (though the scattering compensator 34 is omitted in FIG. 3). As seen from FIG. 4, the scattering compensator 34 is formed such that its thickness in the direction of beam advance varies in a stepwise way in inverse proportion to the thickness of the plane areas of the blade 29. Stated another way, the thickness of the scattering compensator 34 is minimum (i.e., 0) in its region corresponding to the top portion 29A of the blade 29 having the largest thickness and is maximum in its region corresponding to the opening 30. The scattering compensator 34 is made of a material having a comparatively large scattering intensity (i.e., a comparatively large specific gravity), and it has the function of compensating differences in the scattering intensity of the ion beam in the RMW 24. To explain in more detail, when the RMW 24 is arranged on the upstream side in the direction of beam advance as in this embodiment, uniformity of the dose distribution at an irradiation target in the direction perpendicular to the direction of beam advance is reduced due to differences in the scattering intensity of the ion beam, which are caused by differences in the thickness distribution (i.e., the thickness of the plane areas) of the RMW 24 in the direction of beam advance. In this embodiment, however, since the scattering compensator 34 has the thickness in inverse proportion to the thickness of the plane areas of the RMW 24 as described above, the beam scattering intensity corresponding to each plane area of the RMW 24 is made uniform and lowering of the uniformity is overcome (in practice, the beam scattering intensity in each plane area of the RMW 24 is adjusted in consideration of scattering occurred in both the scatterer device 18 and the range adjusting device 19, which are disposed on the downstream side, so that the dose distribution at the irradiation target in the direction perpendicular to the direction of beam advance becomes uniform). Moreover, in this embodiment, the scattering compensator 34 and the RMW 24 serve also as a first scatterer for enlarging the ion beam size. Accordingly, the ion beam having passed through the scattering compensator 34 and the RMW 24 is produced so as to not only spread out the Bragg peak, but also to extend in the direction perpendicular to the direction of beam advance with the scattering.

Returning to FIG. 2, the scattering compensator 34 and the RMW 24 are rotatably supported by the RMW support member 26. The motor 25 for rotating both the scattering compensator 34 and the RMW 24 is also supported by the RMW support member 26 at a position lower than them. The RMW support member 26 is mounted to a support member 37 having a screwed hole (not shown). A ball screw 38 meshes with the screwed hole of the support member 37 in a penetrating relation. The ball screw 38 has an upper end rotatably mounted to the casing 16 and a lower end coupled to an AC servo motor (driving unit) 39 that is mounted to the casing 16. An encoder 40 is coupled to a rotary shaft of the AC serve motor 39. A step motor or a DC servo motor may be used instead of the AC servo motor 39. The AC servo motor 39 and the ball screw 38 constitute a linear actuator for moving the RMW device 17 in the direction of beam advance.

The scatterer device 18 comprises a scatterer 18A and a support member 18B for supporting the scatterer 18A with respect to the casing 16. The scatterer 18A has, e.g., a double ring structure made of materials having different scattering intensities such that the scattering intensity is larger toward the radially inner side and is smaller toward the radially outer side. In other words, the incoming ion beam is scattered at a larger intensity in its radially inner portion and is scattered at a smaller intensity in its radially outer portion. Therefore, the ion beam, of which the dose distribution in the direction perpendicular to the direction of beam advance has been spread to become a normal distribution by the scattering compensator 34 and the RMW 24 serving as the first scatterer, is scattered at a larger intensity in its radially inner portion and is scattered at a smaller intensity in its radially outer portion. As a result, the dose distribution is reduced near a beam center region (i.e., near the beam axis m) and is increased near a beam peripheral region, whereby the dose distribution is adjusted to be uniform in the direction perpendicular to the direction of beam advance.

Figure 5:
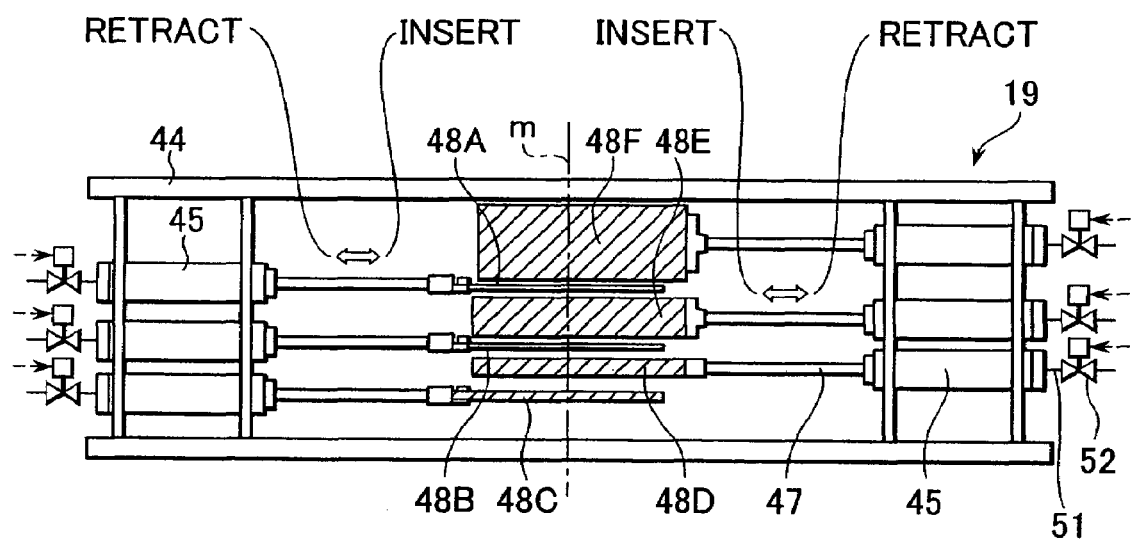
FIG. 5 is a vertical sectional view of a range adjusting device shown in FIG. 2.

The range adjusting device 19 is to adjust the range of the ion beam and has a structure shown in FIG. 5. As seen from FIG. 5, the range adjusting device 19 has a plurality of absorber operating units 45 each comprising a compressive air cylinder 46 and a piston rod 47 that is coupled to a piston (not shown) installed in the compressive air cylinder 46. The absorber operating units 45 are mounted to a support frame 44. The range adjusting device 19 includes a plurality of absorbers 48A to 48F differing in thickness in the direction of beam advance (i.e., in the direction of the beam axis m). Those absorbers are attached to the absorber operating units 45 in a one-to-one relation. Each of the absorbers is made of a resin containing a material having a small atomic number, such as a hydrocarbon. A compressive air pipe 51 having a solenoid valve 52 is connected to the compressive air cylinder 46 of each absorber operating unit 45. The compressive air pipe 51 is connected to a compressive air supply unit (not shown). Further, the absorber operating units 45 of the range adjusting device 19 each have a limit switch. The limit switch of the absorber operating units 45 detects that the corresponding absorber has reached its setting position. Alternatively, the range adjusting device 19 may have a structure having a pair of two wedge-like plates arranged in an opposite relation, each of the wedge-like plates being moved to continuously change the thickness of an overlapped portion.

Returning to FIG. 2, the compensator 20 serves not only to adjust the penetration depth of the ion beam in match with a maximum depth of the diseased part 62 (e.g., the area where a cancer or tumor is generated) in the body of the patient 61 under treatment, but also to adjust the beam range at each position on a plane perpendicular to the direction of beam advance in match with the depthwise shape of the diseased part 62 as the irradiation target. The collimator 21 shapes the ion beam in a planar direction perpendicular to the direction of beam advance so that an irradiation field is collimated in match with the shape of the diseased part 62 in the body of the patient 61.

The particle therapy system of this embodiment further comprises a control system 60 including an irradiation controller (control unit) 54 and motion control systems 56, 57. A memory 55 of the irradiation controller 54 stores irradiation condition information shown in FIG. 6. Items of the irradiation condition information include the position of the diseased part 62 in the depth direction (i.e., the required penetration depth), the type of the scattering compensator 34 and the RMW 24, the incident energy of the irradiation field forming apparatus 15, the thickness of the absorber in the range adjusting device 19 through which the ion beam passes (i.e., the range adjuster thickness), and the distance (Z-axial position) of the scattering compensator 34 and the RMW 24 from an isocenter (irradiation center) in the direction of beam advance. The relationships of the treatment plan information, i.e., the required penetration depth and the incident energy, with respect to the type of the scattering compensator 34 and the RMW 24, the range adjuster thickness, and the Z-axial position of both the scattering compensator 34 and the RMW 24 are determined through calculations and experiments in advance. A treatment planning unit 53 stores various items of treatment plan information (such as the irradiation field size, the incidence direction of the ion beam, the range in the incidence direction, and the incident energy) for the patient 61 to be treated. Instead of separately providing the irradiation controller 54, the motion control systems 56, 57, and the memory 55 from each other, the control system 60 may execute the functions of the irradiation controller 54, the motion control systems 56, 57, and the memory 55 in the incorporated form.

The scattering compensator 34 and the RMW 24 are prepared in plural types as indicated by ID1 to ID9 in FIG. 6. Each of ID1 to ID9 represents No. for identifying each combined unit of the scattering compensator 34 and the RMW 24. Respective combined units of the scattering compensator 34 and the RMW 24 differ, for example, in the height of the RMW 24, the width and height of the plane area 31, the height of the scattering compensator 34, and the width and height of the plane area of the scattering compensator 34. The combined unit of the scattering compensator 34 and the RMW 24 is selected depending on the incident energy inputted to the irradiation field forming apparatus 15, the required penetration depth, the demanded SOBP width, etc., and it is mounted to the RMW support member 26 in advance. In addition, the SOBP width is decided depending on the length of the diseased part 62 in the direction of advance of the ion beam.

Prior to positioning the patient 61 with respect to the irradiation field forming apparatus 15, the irradiation controller 54 receives, from the treatment planning unit 53, the treatment plan information (such as the range (required penetration depth) and the incident energy) for the patient 61, and then stores the received information in the memory 55. That treatment plan information represents the ion beam irradiation conditions. Based on the treatment plan information stored in the memory 55, the irradiation controller 54 selects the unit type of the scattering compensator 34 and the RMW 24 and the range adjuster thickness from among the irradiation condition information. Further, based on the information regarding the selected unit type of the scattering compensator 34 and the RMW 24 and the selected range adjuster thickness, the irradiation controller 54 selects the Z-axial position of the unit of the scattering compensator 34 and the RMW 24. Then, the irradiation controller 54 outputs, to the motion control system 56, the information regarding the selected absorber thickness along with a motion command signal. Based on the information regarding the selected absorber thickness, the motion control system 56 selects one or more absorbers corresponding to the selected absorber thickness from among the absorbers 48A to 48F in the range adjusting device 19. For example, when the thickness of the absorber 48E matches with the selected absorber thickness information, the absorber 48E is selected. The motion control system 56 opens the solenoid valve 52 of the compressive air pipe 51 connected to the relevant absorber operating device 45 for operating the absorber 48E. Compressed air is supplied to the cylinder 46 of the relevant absorber operating device 45, and the absorber 48E is pushed out to the setting position with movement of the piston rod 47. The other absorbers are held in places away from the position of the ion beam passage. When the selected absorber reaches the setting position, a position signal generated upon the operation of the corresponding limit switch is transmitted to the motion control system 56. The motion control system 56 outputs, to the irradiation controller 54, information indicating that the movement of the absorber has completed.

On the other hand, the irradiation controller 54 outputs, to the motion control system 57, the information regarding the Z-axial position of the unit of the scattering compensator 34 and the RMW 24 along with a motion command signal. Based on the Z-axial position information, the motion control system 57 rotates the AC servo motor 39 to move the support member 37 to a predetermined position. Correspondingly, the unit of the scattering compensator 34 and the RMW 24 is moved to the position corresponding to the Z-axial position information. When the motion control system 57 confirms in accordance with a detected signal from the encoder 40 that the support member 37 has reached the desired position, the motion control system 57 outputs, to the irradiation controller 54, information indicating that the movement of the unit of the scattering compensator 34 and the RMW 24 has completed.

After the completion of the preparations described above, the treatment couch 59 is moved such that the center of the diseased part 62 in the body of the patient 61 matches with the isocenter of the irradiation field forming apparatus 15. Then, treatment is started. An operator inputs a treatment start signal from a console (not shown). In response to the treatment start signal, an accelerator controller (not shown) is operated to accelerate the ion beam up to a level of desired energy, and the ion beam is extracted from the synchrotron 4.

The ion beam reaches the irradiation field forming apparatus 15 and advances along the beam axis m in the irradiation field forming apparatus 15. Thus, an irradiation dose distribution in the direction of beam advance is flattened by the unit of the scattering compensator 34 and the RMW 24 (namely, the Bragg peak is spread out by the SOBP device). At the same time, the ion beam is enlarged into a conical form in the direction perpendicular to the direction of beam advance by the unit of the scattering compensator 34 and the RMW 24 serving also as the first scatterer. Thereafter, the ion beam passes through the scatterer 18A of the scatterer device 18, whereby a dose distribution in the direction perpendicular to the direction of beam advance is flattened. The ion beam then passes through one or more absorbers of the range adjusting device 19, whereby the beam energy is reduced and the range of the ion beam in the patient body is adjusted. After passing through the range adjusting device 19, the ion beam passes through the compensator 20, whereby the range is adjusted in match with the shape of the diseased part 62 in the direction of beam advance. The ion beam then passes through the aperture collimator 21, whereby the ion beam is collimated so as to have a shape in match with the shape of the diseased part 62 in the direction perpendicular to the direction of beam advance. In this way, the ion beam is irradiated to the diseased part 62 while forming a high-dose filed concentrated on an area of the diseased part to be treated.

With the construction described above, this embodiment operates as follows.

Figure 7A:
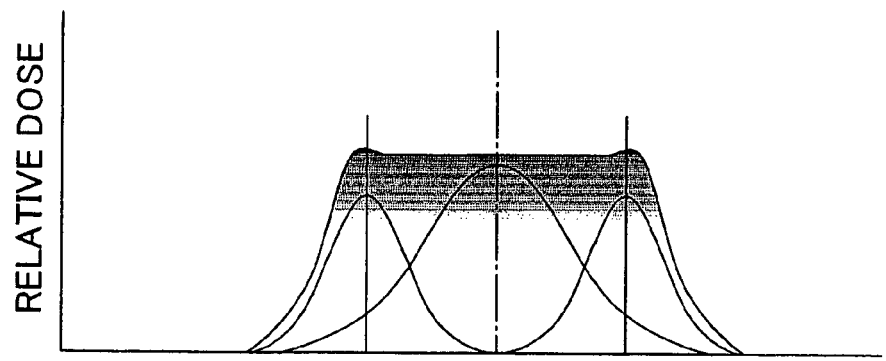
Figure 7B:
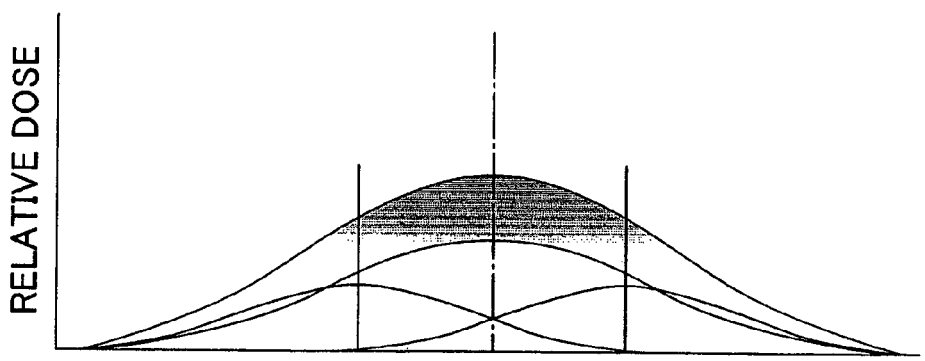
Figure 7C:
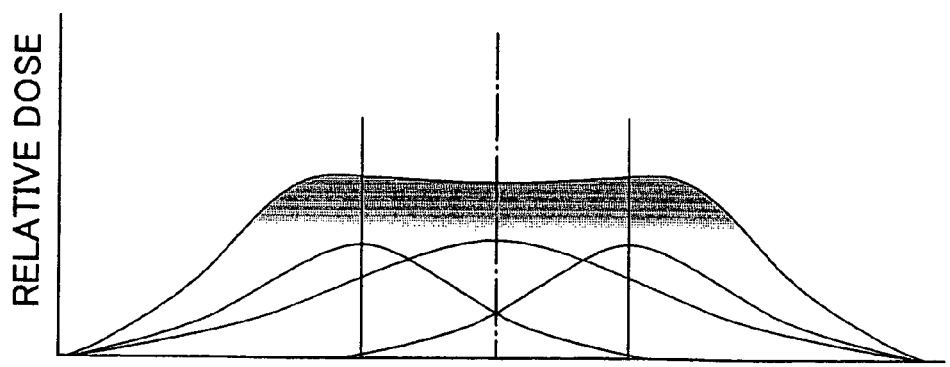

When the scattering intensity of the ion beam in the RMW device 17 (i.e., the unit of the scattering compensator 34 and the RMW 24 serving also as the first scatterer) and the scattering intensity in the scatterer device 18 are in balance, the dose distribution at the irradiation target in the direction perpendicular to the direction of beam advance becomes uniform, as shown in FIG. 7A, and therefore the high-dose filed concentrated on the diseased part area can be formed. Generally, a charged particle beam has a feature that the higher incident energy, the smaller is the scattering intensity when the beam passes through a material, and the lower incident energy, the larger is the scattering intensity. Therefore, when the incident energy of the ion beam is changed from the scattering balanced state shown in FIG. 7A, the scattering balance is lost and the dose distribution in the direction perpendicular to the direction of beam advance is disturbed. For example, when the incident energy of the ion beam is reduced, the scattering intensity in the unit of the scattering compensator 34 and the RMW 24 and the scattering intensity in the scatterer device 18 are both increased. Hence, in the related art in which the unit of the scattering compensator 34 and the RMW 24 is held fixed, the scattering balance is lost and the dose distribution at the irradiation target is disturbed, as shown in FIG. 7B, such that the dose near a beam central region is larger than the dose near a beam peripheral region. According to this embodiment, when the incident energy is reduced from 250 MeV to 200 MeV, for example, as shown in FIG. 6, the unit type of the scattering compensator 34 and the RMW 24 is changed from ID1 to ID3, and the unit of the scattering compensator 34 and the RMW 24 is moved toward the upstream side in the direction of beam advance from the Z-axial position of 3060 mm to 3072 mm (on assumption that the range adjuster thickness is 0). With such an adjustment, the size of the ion beam entering the scatterer 18A of the scatterer device 18 is enlarged, and the intensity of the irradiated beam can be increased in its radially outer region where the scattering intensity is comparatively small. As a result, the dose near the beam central region decreases and the dose near the beam peripheral region increases, whereby the dose distribution in the direction perpendicular to the direction of beam advance can be made uniform as shown in FIG. 7C. On the other hand, when the incident energy of the ion beam is increased from the scattering balanced state, the dose distribution in the concave form is resulted in which the dose near the beam central region is smaller than the dose near the beam peripheral region. According to this embodiment, therefore, the unit of the scattering compensator 34 and the RMW 24 is moved toward the downstream side in the direction of beam advance to reduce the size of the ion beam entering the scatterer 18A of the scatterer device 18, thereby increasing the intensity of the irradiated beam in its radially inner region where the scattering intensity is comparatively large. As a result, the dose near the beam central region increases and the dose near the beam peripheral region decreases, whereby the dose distribution in the direction perpendicular to the direction of beam advance can be made uniform.

The ion beam is also scattered by the absorbers 48A to 48F of the range adjusting device 19. Therefore, when the thickness of the absorber of the range adjusting device 19 placed in the beam path (i.e., the range adjuster thickness) is changed from the scattering balanced state among the unit of the scattering compensator 34 and the RMW 24, the scatterer device 18, and the range adjusting device 19, the scattering balance is lost and the dose distribution in the direction perpendicular to the direction of beam advance is disturbed. For example, when the range adjuster thickness is increased, the scattering intensity of the ion beam in the range adjusting device 19 is increased. Hence, in the related art in which the unit of the scattering compensator 34 and the RMW 24 is held fixed, the scattering balance is lost and the dose distribution at the irradiation target in the direction perpendicular to the direction of beam advance is disturbed, as shown in FIG. 7B, such that the dose near the beam central region is larger than the dose near the beam peripheral region. According to this embodiment, when the range adjuster thickness is increased from 0 cm to 6.0 cm, for example, as shown in FIG. 6 on condition of the incident energy being 250 MeV, the unit of the scattering compensator 34 and the RMW 24 is moved toward the upstream side in the direction of beam advance from the Z-axial position of 3060 mm to 3120 mm. With such an adjustment, the size of the ion beam entering the scatterer 18A of the scatterer device 18 is enlarged, and the intensity of the irradiated beam can be increased in its radially outer region where the scattering intensity is comparatively small. As a result, the dose near the beam central region decreases and the dose near the beam peripheral region increases, whereby the dose distribution in the direction perpendicular to the direction of beam advance can be made uniform as shown in FIG. 7C. On the other hand, when the range adjuster thickness is reduced from the scattering balanced state, the dose distribution in the concave form is resulted in which the dose near the beam central region is smaller than the dose near the beam peripheral region. According to this embodiment, therefore, the unit of the scattering compensator 34 and the RMW 24 is moved toward the downstream side in the direction of beam advance to reduce the size of the ion beam entering the scatterer 18A of the scatterer device 18, thereby increasing the intensity of the irradiated beam in its radially inner region where the scattering intensity is comparatively large. As a result, the dose near the beam central region increases and the dose near the beam peripheral region decreases, whereby the dose distribution in the direction perpendicular to the direction of beam advance can be made uniform.

With this embodiment, as described above, by moving the unit of the scattering compensator 34 and the RMW 24 in the direction of beam advance to be located at the setting position depending on the incident energy and the range adjuster thickness, a balance in scattering density among the unit of the scattering compensator 34 and the RMW 24, the scatterer device 18, and the range adjusting device 19 can be adjusted so that the dose distribution at the irradiation target in the direction perpendicular to the direction of beam advance is more uniform.

Also, with this embodiment, by providing the scattering compensator 34 integrally with the RMW 24, the RMW device 17 can be arranged on the upstream side in the direction of beam advance. More specifically, when the RMW device 17 is arranged on the downstream side in the direction of beam advance, there is a demerit that the effective beam distance up to the diseased part 62, i.e., the irradiation position, reduces and a blur (penumbra) in the dose distribution spreading beyond the irradiation target increases correspondingly. In contrast, with this embodiment, since the RMW device 17 is arranged on the upstream side in the direction of beam advance, the penumbra can be reduced.

Further, by providing the scattering compensator 34 integrally with the RMW 24, it is possible to shorten the distance between by the scattering compensator 34 having a high scattering intensity and the RMW 24 as compared with the case of separately providing those two components from each other, and hence to reduce the size of the RMW 24. In addition, by providing the scattering compensator 34 integrally with the RMW 24, the number of driving sources, such as the AC servo motors 39, (i.e., the number of linear actuators) can be reduced.

Second Embodiment

Figure 8:
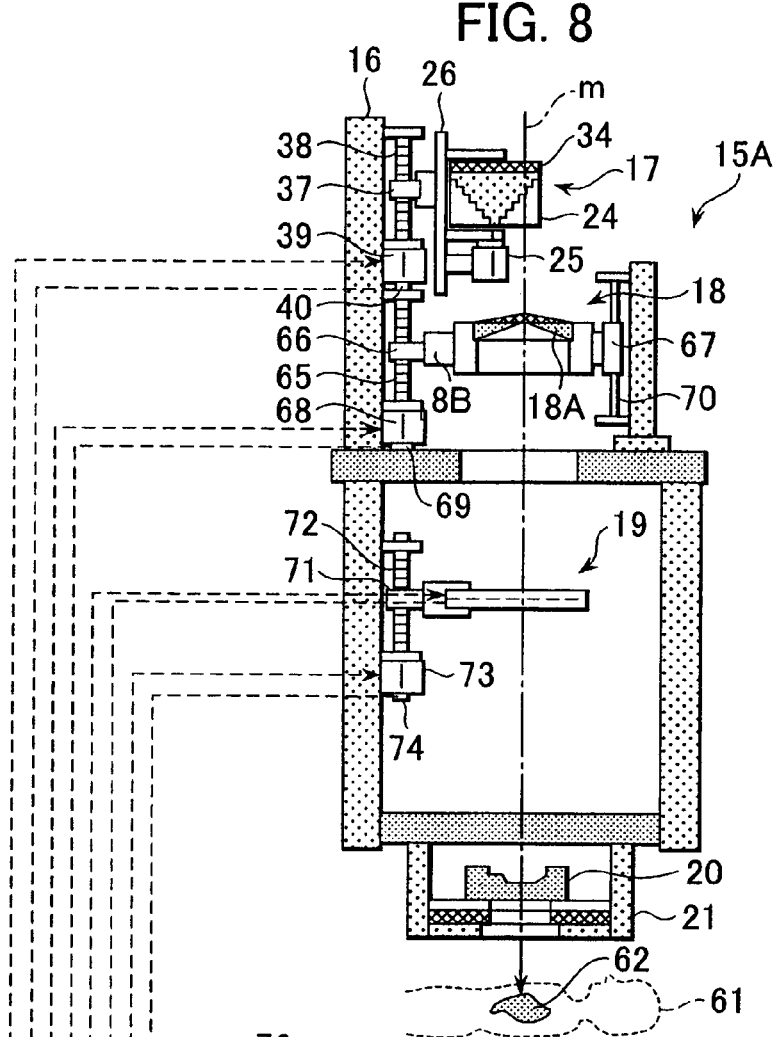
FIG. 8 is a vertical sectional view of an irradiation field forming apparatus of a particle therapy system according to another preferable embodiment, i.e., a second embodiment, of the present invention.
Figure 8:
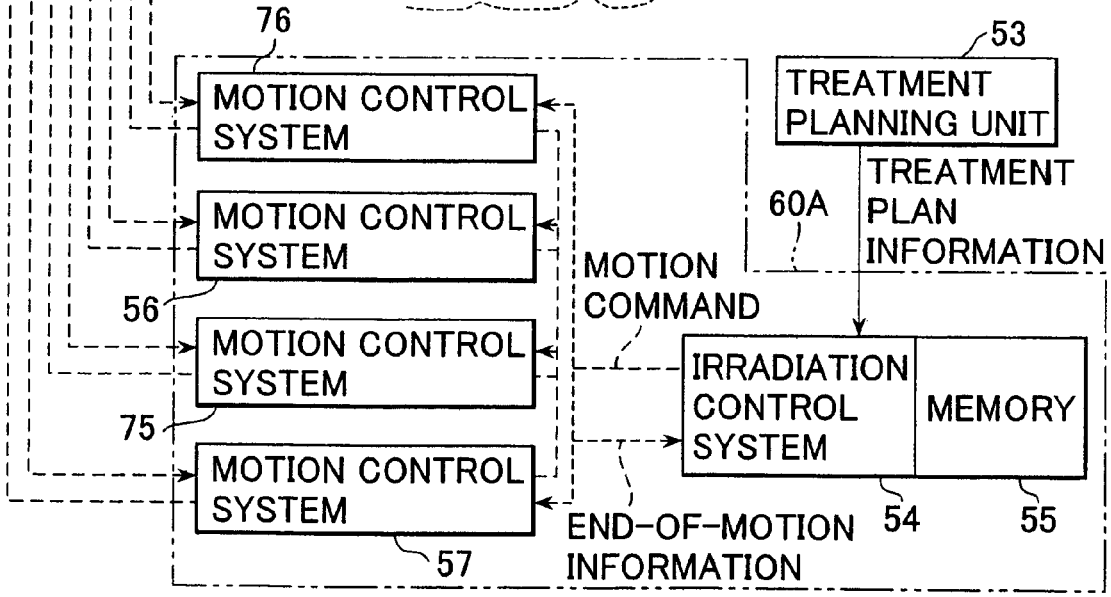

An particle therapy system according to another preferable embodiment, i.e., a second embodiment, of the present invention will be described below. The particle therapy system of this embodiment differs from the particle therapy system 1, shown in FIG. 1, in that the irradiation field forming apparatus 15 and the control system 60 are replaced respectively with the irradiation field forming apparatus 15A and the control system 60A shown in FIG. 8. In the irradiation field forming apparatus 15A of this embodiment, the scatterer device 18 and the range adjusting device 19 are movable in the direction of beam advance in addition to the RMW device 17. More specifically, a support member 18B of the scatterer device 18 is mounted to a support member 66 having a screwed hole (not shown) in mesh with a ball screw 65 and also to a support member 67 having through hole (not shown). The ball screw 65 has an upper end rotatably mounted to the casing 16 and a lower end coupled to an AC servo motor 68 that is mounted to the casing 16. An encoder 69 is coupled to a rotary shaft of the AC serve motor 68. The support member 67 is movably attached to a linear guide 70 that is also mounted to the casing 16. The AC servo motor 68, the ball screw 65, and the linear guide 70 constitute a linear actuator for moving the scatterer device 18 in the direction of beam advance.

Further, the range adjusting device 19 is mounted to a support member 71 having a screwed hole (not shown). A ball screw 72 meshes with the screwed hole of the support member 71 in a penetrating relation. The ball screw 72 has an upper end rotatably mounted to the casing 16 and a lower end coupled to an AC servo motor 73 that is mounted to the casing 16. An encoder 74 is coupled to a rotary shaft of the AC serve motor 73. The AC servo motor 73 and the ball screw 72 constitute a linear actuator for moving the range adjusting device 19 in the direction of beam advance.

In the control system 60A of this embodiment, the memory 55 of the irradiation controller 54 stores, in addition to the items of the irradiation condition information shown in FIG. 6, the respective distances (Z-axial positions) of the scatterer device 18 and the range adjusting device 19 from the isocenter (irradiation center) in the direction of beam advance. The relationships of the treatment plan information, i.e., the required penetration depth and the incident energy, with respect to the Z-axial positions of the scatterer device 18 and the range adjusting device 19 are determined through calculations and experiments in advance. Based on the treatment plan information from the treatment planning unit 53, the irradiation controller 54 selects the unit type of the scattering compensator 34 and the RMW 24 and the range adjuster thickness from among the irradiation condition information. Further, based on the information regarding the selected unit type of the scattering compensator 34 and the RMW 24 and the selected range adjuster thickness, the irradiation controller 54 selects the respective Z-axial positions of the scatterer device 18 and the range adjusting device 19 in addition to the Z-axial position of the unit of the scattering compensator 34 and the RMW 24.

The control system 60A of this embodiment comprises motion control systems 75, 76 in addition to the motion control systems 56, 57. The irradiation controller 54 outputs, to the motion control system 75, the information regarding the Z-axial position of the scatterer device 18 along with a motion command signal. Based on the information regarding the information regarding the Z-axial position of the scatterer device 18, the motion control system 75 rotates the AC servo motor 68 to move the support member 66 to a predetermined position. Correspondingly, the scatterer device 18 is moved to the position corresponding to the above Z-axial position information. When it is confirmed in accordance with a detected signal from the encoder 69 that the support member 66 has reached the predetermined position, the motion control system 75 outputs, to the irradiation controller 54, information indicating the end of movement of the scatterer device 18. On the other hand, the irradiation controller 54 outputs, to the motion control system 76, the information regarding the Z-axial position of the range adjusting device 19 along with a motion command signal. Based on the information regarding the information regarding the Z-axial position of the range adjusting device 19, the motion control system 76 rotates the AC servo motor 73 to move the support member 71 to a predetermined position. Correspondingly, the range adjusting device 19 is moved to the position corresponding to the above Z-axial position information. When it is confirmed in accordance with a detected signal from the encoder 74 that the support member 71 has reached the predetermined position, the motion control system 57 outputs, to the irradiation controller 54, information indicating the end of movement of the range adjusting device 19.

With this embodiment thus constructed, it is possible to not only obtain a uniform dose distribution in the direction perpendicular to the direction of beam advance as in the first embodiment, but also to adjust the effective beam distance in the irradiation field forming apparatus. More specifically, in the first embodiment in which only the unit of the scattering compensator 34 and the RMW 24 is moved, since the effective beam distance in the irradiation field forming apparatus varies when the unit of the scattering compensator 34 and the RMW 24 is moved, the treatment pouch 59 must be moved for proper positioning, and the compensator 20, etc. must be replaced. In this embodiment, when the unit of the scattering compensator 34 and the RMW 24, the scatterer device 18 and the range adjusting device 19 are also moved in the direction of beam advance to be arranged in the respective predetermined positions so that the effective beam distance can be adjusted constant. The operations for positioning the treatment pouch 59 and replacing the compensator 20, etc. can be thereby eliminated. As a result, the treatment time can be prevented from being prolonged.

Also, with this embodiment, since the effective beam distance is adjustable as described above, the effective beam distance can be adjusted to become longer than that in the first embodiment by arranging the unit of the scattering compensator 34 and the RMW 24, the scatterer device 18, and the range adjusting device 19 at respective predetermined positions. It is hence possible to not only obtain a uniform dose distribution in the direction perpendicular to the direction of beam advance as in the first embodiment, but also to further reduce a blur (penumbra) in the irradiation dose distribution spreading beyond the irradiation target.

Moreover, with this embodiment, the effective beam distance can be adjusted to become shorter on the contrary to the above case. In the first embodiment described above, by moving the unit of the scattering compensator 34 and the RMW 24 in the direction of beam advance, the non-uniform dose distribution as shown in FIG. 7B can be adjusted to the uniform dose distribution as shown in FIG. 7C. However, because the distance from the unit of the scattering compensator 34 and the RMW 24 to the scatterer device 18 increases, the beam size is enlarged correspondingly with scattering in the direction perpendicular to the direction of beam advance as compared with the original dose distribution shown in FIG. 7A. With this embodiment, by arranging the unit of the scattering compensator 34 and the RMW 24, the scatterer device 18, and the range adjusting device 19 at respective predetermined positions, it is hence possible to not only obtain a uniform dose distribution in the direction perpendicular to the direction of beam advance as in the first embodiment, but also to adjust the beam size at the irradiation target to an optimum size. Consequently, efficiency in utilization of the ion beam can be further increased, and the irradiation dose can be increased.

While each of the above-described embodiments aims an application to the particle therapy system including the synchrotron, the irradiation field forming apparatus according to each embodiment is also applicable to a particle therapy system including a cyclotron.

Also, while each of the above-described embodiments uses the RWM as the Bragg peak spreading-out device, a ridge filter can also be used instead of the RMW. The case of using a ridge filter can provide similar advantages to those in each of the above-described embodiments.

Additionally, each of the above-described embodiments can be further applied to a material irradiation system for irradiating a charged particle beam to materials, a food irradiation system for irradiating a charged particle beam to foods, and a radio isotope producing system utilizing a charged particle beam, each of those apparatuses comprising a charged particle beam generator and an irradiation field forming apparatus.

What is claimed is:

1. A method of adjusting an irradiation field forming apparatus comprising a Bragg peak spreading-out device for spreading out a Bragg peak of a charged particle beam extracted from a charged particle beam generator, and a scattering compensator provided on said Bragg peak spreading-out device and compensating differences in scattering intensity of the charged particle beam in said Bragg peak spreading-out device, thereby irradiating the charged particle beam to an irradiation target, wherein said method includes a step of, prior to extracting the charged particle beam, moving at least one of said Bragg peak spreading-out device and said scattering compensator in a direction of advance of the charged particle beam to a predetermined position.

2. A method of adjusting an irradiation field forming apparatus according to claim 1, wherein said method further includes a step of moving at least one of said Bragg peak spreading-out device and said scattering compensator in the direction of advance of the charged particle beam depending on incident energy of the charged particle beam.

3. A method of adjusting an irradiation field forming apparatus according to claim 1, wherein said method further includes a step of moving at least one of said Bragg peak spreading-out device and said scattering compensator in the direction of advance of the charged particle beam depending on a thickness of a portion of said range adjusting device through which the charged particle beam passes.

4. A method of adjusting an irradiation field forming apparatus comprising a Bragg peak spreading-out device for spreading out a Bragg peak of a charged particle beam extracted from a charged particle beam generator, a scattering compensator provided on said Bragg peak spreading-out device and compensating differences in scattering intensity of the charged particle beam in said Bragg peak spreading-out device, a scatterer device through which the charged particle beam passes, and a range adjusting device for changing a range of the charged particle beam, thereby irradiating the charged particle beam to an irradiation target, wherein said method includes a step of, prior to extracting the charged particle beam, moving at least one of said Bragg peak spreading-out device and said scattering compensator in a direction of advance of the charged particle beam to a predetermined position.

5. A method of adjusting an irradiation field forming apparatus according to claim 4, wherein said method further includes a step of moving at least one of said Bragg peak spreading-out device and said scattering compensator in the direction of advance of the charged particle beam depending on incident energy of the charged particle beam.

6. A method of adjusting an irradiation field forming apparatus according to claim 4, wherein said method further includes a step of moving at least one of said Bragg peak spreading-out device and said scattering compensator in the direction of advance of the charged particle beam depending on a thickness of a portion of said range adjusting device through which the charged particle beam passes.

* * * * *